United States Patent [19]

Scapini et al.

[11] 4,264,770
[45] Apr. 28, 1981

[54] PROCESS FOR PREPARING 1,4-BIS-PIPERONYLPIPERAZINE AND SIMILAR COMPOUNDS

[75] Inventors: Giancarlo Scapini, Bologna; Gian P. Gardini, Parma; Armando Raimondi, Anagni; Placido Poidomani, Rome, all of Italy

[73] Assignee: Farmaceutici Geymonat Sud S.P.A., Anagni, Italy

[21] Appl. No.: 34,040

[22] Filed: Apr. 27, 1979

[30] Foreign Application Priority Data

Apr. 27, 1978 [IT] Italy .............................. 67951 A/78

[51] Int. Cl.³ .......................................... C07D 405/14
[52] U.S. Cl. ................... 544/377; 544/402; 544/403
[58] Field of Search ..................... 544/377, 403, 402

[56] References Cited

U.S. PATENT DOCUMENTS

| | | | |
|---|---|---|---|
| 2,415,786 | 2/1947 | Buck et al. ........................... | 544/402 |
| 2,695,294 | 11/1954 | Swain ................................... | 544/377 |
| 2,870,152 | 1/1959 | Schusteritz et al. ................ | 544/403 |
| 2,887,488 | 5/1959 | Smiley ................................. | 544/402 |
| 3,119,826 | 1/1964 | Regnier et al. ..................... | 544/377 |

OTHER PUBLICATIONS

Cordes et al., "Kinetics of Organic Reactions in Micellary Systems", Accad. Chem. Res. 2 (1969), pp. 329–337.

*Primary Examiner*—Paul M. Coughlan, Jr.
*Attorney, Agent, or Firm*—Sughrue, Rothwell, Mion, Zinn and Macpeak

[57] ABSTRACT

Compounds of general formula:

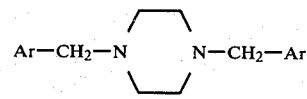

particularly 1,4-bis-piperonylpiperazine, are obtained with high yields by reacting equimolar quantities of piperazine and of a chloride Ar—CH₂—Cl in the presence of water, under agitation, and in the presence of a cationic surfactant.

23 Claims, No Drawings

PROCESS FOR PREPARING 1,4-BIS-PIPERONYLPIPERAZINE AND SIMILAR COMPOUNDS

The present invention relates to the preparation of 1,4-bis-piperonylpiperazine and similar compounds having the general formula:

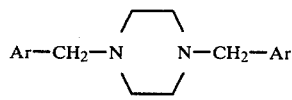  (I)

in which Ar is a benzene ring, either substituted or unsubstituted. As is known, in the case of 1,4-bis-piperonylpiperazine, the Ar substituent is 3,4-methylenedioxyphenyl:

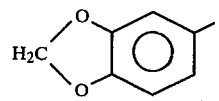  (II)

Generally, the benzene ring may be mono-, di- or tri-substituted and the following substituents may be cited by way of example:
- a halogen atom, preferably chlorine atom,
- a lower alkyl radical, preferably methyl radical,
- a dialkylamino group wherein the alkyls are lower alkyls, the "lower alkyl" being an alkyl group comprising 1 to 4 carbon atoms.

These compounds, which are particularly useful as antitussive medicines, are described in Belgian Pat. No. 616,371 of the Apr. 12, 1962, wherein further substituents on the benzene ring are also indicated. Example 1 of this prior patent describes preparation of piperonylpiperazine, from which 1,4-bis-piperonylpiperazine is obtained by a method described in Example 5. The reaction steps described are long and expensive. Moreover, the yield from the first reaction step (piperonylpiperazine) is about 35%, the yield from the second reaction step (Example 5) is about 30%, whereby the total yield is as low as about 10%.

According to the invention, 1,4-bis-piperonylpiperazine and other compounds of formula (I) may be obtained quickly, with low cost and high yield, by making use of the micellary catalysis exerted by cationic surfactants.

The invention, therefore, provides a process for the preparation of compounds of formula (I), characterised by the steps of reacting at elevated temperature equimolecular quantities of piperazine and of the chloride Ar—CH₂—Cl (in which Ar is as indicated above) in the presence of water, under agitation, and in the presence of a catalytic quantity of a cationic surface-active agent and recovering the compound (I) from the reaction mixture.

The piperazine may be used in its anhydrous or hydrated (hexahydrate) form. When piperazine hexahydrate is used, no added water is necessary to assure the presence of water in the reaction mixture as the hydration water is sufficient to secure micellary catalysis condition. When anhydrous piperazine is used, the presence of water is secured by addition of a limited amount distilled water, preferably corresponding to hexahydrate proportion (6 moles water per 1 mole anhydrous piperazine).

The reaction is preferably carried out at 100°–130° C. The surface-active agent is conveniently the bromide or chloride of cetyl-trimethyl-ammonium.

By reacting piperazine with piperonyl chloride:

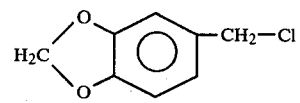  (III)

1,4-bis-piperonylpiperazine is obtained, with the by-product piperazine dihydrochloride, according to the general reaction:

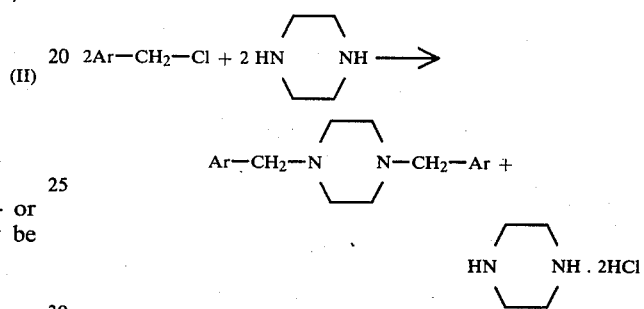

The reaction time is of the order of 1–2 hours. Initially the reaction is noticeably exothermic, whereby external cooling is necessary to maintain the temperature of the reaction mass under 130° C., preferably between 100° C. and 110° C., in this stage. Once this exothermic stage is terminated, the temperature is maintained within the range of from 100°–110° C. to 130° C.±5° C. by an external heating bat. Evaporation is prevented by the reflux condenser. At the end of the reaction and after cooling, a solid or oily mass is obtained from which the product (I) may be recovered without any particular difficulty. The yield is very high, greater than 80% of the theoretical. Recovery of the product (I) from the reaction mass is preferably done by dissolving the product from the mass in aqueous caustic soda, extracting the product from the obtained alkaline solution by means of a volatile organic inert solvent, and evaporating the solvent from the organic phase (extract phase) to obtain a solid residue which may be crystallized from another solvent, preferably ethanol.

EXAMPLE

Preparation of 1,4-bis-piperonylpiperazine

The following reagents are loaded into a 250 ml flask provided with a stirrer, a thermometer and a reflux condenser: 25.8 g (0.3 moles) of anhydrous piperazine and 32.5 ml (1.8 moles) of distilled water, or simply 58.3 g (0.3 moles) of piperazine hexahydrate, and 51.2 g (0.3 moles) of piperonyl chloride. The mixture is stirred vigorously, 2 g of cetyl-trimethyl-ammonium bromide are added and the flask is cooled with water so that the temperature of the stirred reaction mass does not rise above 110° C. Once the exothermic stage is terminated, the temperature is maintained at 130° C.±5° C. by means of an external oil bath for 90 minutes, under agitation.

After cooling, a solid mass is obtained which is taken up in 400 ml of an aqueous solution containing 10% by weight of caustic soda to dissolve the product from the mass. The alkaline solution obtained is extracted twice with 500 ml of chloroform. The organic phase is washed with water and then evaporated to dryness. The residue is crystallized from ethanol 96% strength.

50.5 g (theoretical value 53.18) of pale-yellowish white crystals are obtained with a melting point of 155°-156° C. The yield is 95% of the theoretical. In agreement with the above Belgium Patent, the dihydrochloride melts with decomposition above 260° C.

Analysis for $C_{20}H_{22}N_2O_4$: Calc.% C 67.78, H 6.26, N 7.90; Found% 67.52, 6.25, 7.97.

The following products were also obtained by the method described in the Example:

(1) 1,4-bis-benzylpiperazine (Ar=$C_6H_5$—) with practically theoretical yield; m.p. 91°-92° C. (crystallized from 96% ethanol);

(2) 1,4-bis-(4'-methylbenzyl)piperazine (Ar=p-$CH_3$—$C_6H_4$—) with 96% yield; m.p. 180°-181° C. (crystallized from 96% ethanol);

(3) 1,4-bis-(2'-chlorobenzyl)-piperazine (Ar=o-Cl—$C_6H_4$—) with 91% yield; m.p. 101°-102° C. (crystallized from 95% ethanol);

(4) 1,4-bis-(4'-dimethylaminobenzyl)-piperazine (Ar=p-$(CH_3)_2$N—$C_6H_4$—) with 87% yield m.p. 180°-181° C. (crystallized from ethyl acetate);

(5) 1,4-bis-(4'-diethylaminobenzyl)-piperazine (Ar=p-$(C_2H_5)_2$N—$C_6H_4$—) with 84% yield; m.p. 110°-111° (crystallized from n-hexane).

We claim:

1. A process for preparing a compound having the formula:

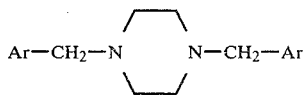

wherein Ar is selected from the group consisting of (1) mono-, di-, and tri-substituted benzene rings in which the substituents are members of the group consisting of halogen atoms, lower alkyl radicals and di (lower alkyl) amino groups, (2) an unsubstituted benzene ring and (3) 3,4-methylenedioxyphenyl comprising the steps of reacting piperazine and a chloride Ar—$CH_2$—Cl, wherein Ar has the meaning indicated above, in the presence of water and an HCl acceptor, under agitation and in the presence of a catalytically effective amount of a cationic surfactant which exerts a micellary catalytic effect, and recovering the compound from the reaction mass.

2. A process according to claim 1, wherein the chloride Ar—$CH_2$—Cl is piperonyl chloride.

3. A process according to claim 1, wherein Ar is p-$CH_3C_6H_4$—.

4. A process according to claim 1, wherein Ar is o-Cl—$C_6H_4$—.

5. A process according to claim 1, wherein Ar is p-$(CH_3)_2$N—$C_6H_4$—.

6. A process according to claim 1, wherein Ar is p-$(C_2H_5)_2$N—$C_6H_4$—.

7. A process according to claims 1, 2, 3, 4, 5 or 6, wherein the surfactant is the bromide or chloride of cetyl-trimethyl-ammonium.

8. A process according to claims 1, 2, 3, 4, 5 or 6, wherein the reaction temperature is from 100° C. to 130° C.

9. A process according to claim 1, wherein the compound is recovered from the reaction mass by dissolving the compound from the mass in aqueous caustic soda, extracting the compound from its alkaline solution by means of a volatile organic inert solvent, and evaporating the solvent from the extract.

10. The process of claim 1, wherein said HCl acceptor is piperazine added in stoichiometric excess.

11. A process for preparing 1,4-bis-piperonylpiperazine comprising the steps of: mixing together piperonyl chloride and a molar proportion of (a) piperazine hexahydrate or (b) anhydrous piperazine accompanied by an amount of water at least approximately corresponding to hydration water of the hexahydrate; adding to the mixture a catalytically effective amount of a micelle-forming surfactant which exerts micellary catalytic effect while stirring and cooling the mixture to keep its temperature in the range of 100° C. to 130° C.; once the exothermic heat development is terminated, continuing stirring the mixture while keeping the latter at a temperature of from 100° C. to about 130° C. by heating until the reaction is terminated; cooling the reacted mass; dissolving from the cooled mass the 1,4-bis-piperonylpiperazine by means of aqueous caustic soda; extracting the obtained alkaline solution with a volatile organic inert solvent; and recovering the 1,4-bis-piperonyl-piperazine from the organic extraction phase by evaporating the solvent.

12. A process according to claim 11, wherein the surfactant is the bromide or chloride of cetyl-trimethyl-ammonium.

13. A process as claimed in claim 12, wherein said cooling of the mixture is effected so as to keep the temperature of the mixture in the range of from 100° C. to 110° C.

14. A process for preparing a compound having the formula:

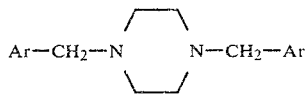

wherein Ar is selected from the group consising of (1) mono-, di-, and tri-substituted benzene rings in which the substituents are members of the group consisting of halogen atoms, lower alkyl radicals and di (lower alkyl) amino groups, (2) an unsubstituted benzene ring and (3) 3,4-methylenedioxyphenyl comprising the steps of reacting piperazine and a chloride Ar—$CH_2$—Cl, wherein Ar has the meaning indicated above, in the presence of water and an HCl acceptor, under agitation and in the presence of a catalytically effective amount of the bromide or chloride of cetyl-trimethyl-ammonium as a cationic surfactant which exerts a micellary catalytic effect, and recovering the compound from the reaction mass.

15. A process according to claim 14, wherein the chloride Ar—$CH_2$—Cl is piperonyl chloride.

16. A process according to claim 14, wherein Ar is p-$CH_3C_6H_4$.

17. A process according to claim 14, wherein Ar is o-Cl—$C_6H_4$.

18. A process according to claim 14, wherein Ar is p-(CH$_3$)$_2$ N—C$_6$H$_4$.

19. A process according to claim 14, wherein Ar is p-(C$_2$H$_5$)$_2$ N—C$_6$H$_4$.

20. A process according to claims 14, 15, 16, 17, 18 or 19, wherein the reaction temperature is from 100° C. to 130° C.

21. A process according to claim 14, wherein the compound is recovered from the reaction mass by dissolving the compound from the mass in aqueous caustic soda, extracting the compound from its alkaline solution by means of a volatile organic inert solvent, and evaporating the solvent from the extract.

22. A process for preparing 1,-4-bis-piperonylpiperazine comprising the steps of: mixing together piperonyl chloride and a molar proportion of (a) piperazine hexahydrate or (b) anhydrous piperazine accompanied by an amount of water at least approximately corresponding to hydration water of the hexahydrate; adding to the mixture a catalytically effective amount of the bromide or chloride of cetyl-trimethyl-ammonium as a micelle-forming surfactant which exerts a micellary catalytic effect while stirring and cooling the mixture to keep its temperature in the range of 100° C. to 130° C.; once the exothermic heat development is terminated, continuing stirring the mixture while keeping the latter at a temperature of from 100° C. to about 130° C. by heating until the reaction is terminated; cooling the reacted mass; dissolving from the cooled mass the 1,4-bispiperonyl-piperazine by means of aqueous caustic soda; extracting the obtained alkaline solution with a volatile organic inert solvent; and recovering the 1,4-bis-piperonyl-piperazine from the organic extraction phase by evaporating the solvent.

23. A process as claimed in claim 22, wherein said cooling of the mixture is effected so as to keep the temperature of the mixture in the range of from 100° C. to 110° C.

* * * * *